United States Patent [19]

Puls et al.

[11] 4,200,692

[45] Apr. 29, 1980

[54] PROCESS FOR THE PRODUCTION OF XYLOSE BY ENZYMATIC HYDROLYSIS OF XYLAN

[75] Inventors: Jürgen Puls, Pinneberg; Michael Sinner, Dassendorf; Hans-Hermann Dietrichs, Reinbek, all of Fed. Rep. of Germany

[73] Assignee: Projektierung Chemische Verfahrenstechnik GmbH, Ratingen, Fed. Rep. of Germany

[21] Appl. No.: 836,713

[22] Filed: Sep. 26, 1977

[30] Foreign Application Priority Data

Sep. 29, 1976 [DE] Fed. Rep. of Germany ....... 2643800

[51] Int. Cl.[2] .............................................. C12P 19/14

[52] U.S. Cl. ...................................... 435/99; 435/174; 435/176; 435/814

[58] Field of Search ................... 195/31 R, 33, 13, 63, 195/68, 115, 116, DIG. 11, 66 R, 62; 435/99, 176, 174, 814

[56] References Cited

FOREIGN PATENT DOCUMENTS 7112936 4/1971 Japan .................................... 195/31 R 7121788 6/1971 Japan .................................... 195/31 R 7215743 5/1972 Japan .................................... 195/66 R

OTHER PUBLICATIONS

Puls et al., "Carrier Bound Xylanases", *Chem. Abstracts*, vol. 81, No. 19, (1974), p. 215, Abs. #116603a.

Hashimoto et al., "Fractionation of Subunits in Xylanases from *Trichoderma Viride* with a New Simple Preparative Polyacrylamide Gel Electrophoresis Apparatus", *Agr. Biol. Chem.*, vol. 40, No. 3, (1976), pp. 635-636.

Blatt, "Ultrafiltration for Enzyme Concentration", *Methods in Enzymology*, vol. XXII, Jakoby ed., Academic Press, New York (1971), pp. 39-49.

*Primary Examiner*—Thomas G. Wiseman

*Attorney, Agent, or Firm*—Schwartz, Jeffery, Schwaab, Mack, Blumenthal & Koch

[57] ABSTRACT

A process for the production of xylose by enzymatic hydrolysis of xylan wherein an aqueous solution containing xylan is treated with a carrier having bonded thereto xylanase enzyme and a carrier having bonded thereto β-xylosidase and, optionally, uronic acid-splitting enzyme.

8 Claims, 3 Drawing Figures

PROCESS FOR THE PRODUCTION OF XYLOSE BY ENZYMATIC HYDROLYSIS OF XYLAN

Figure 1:
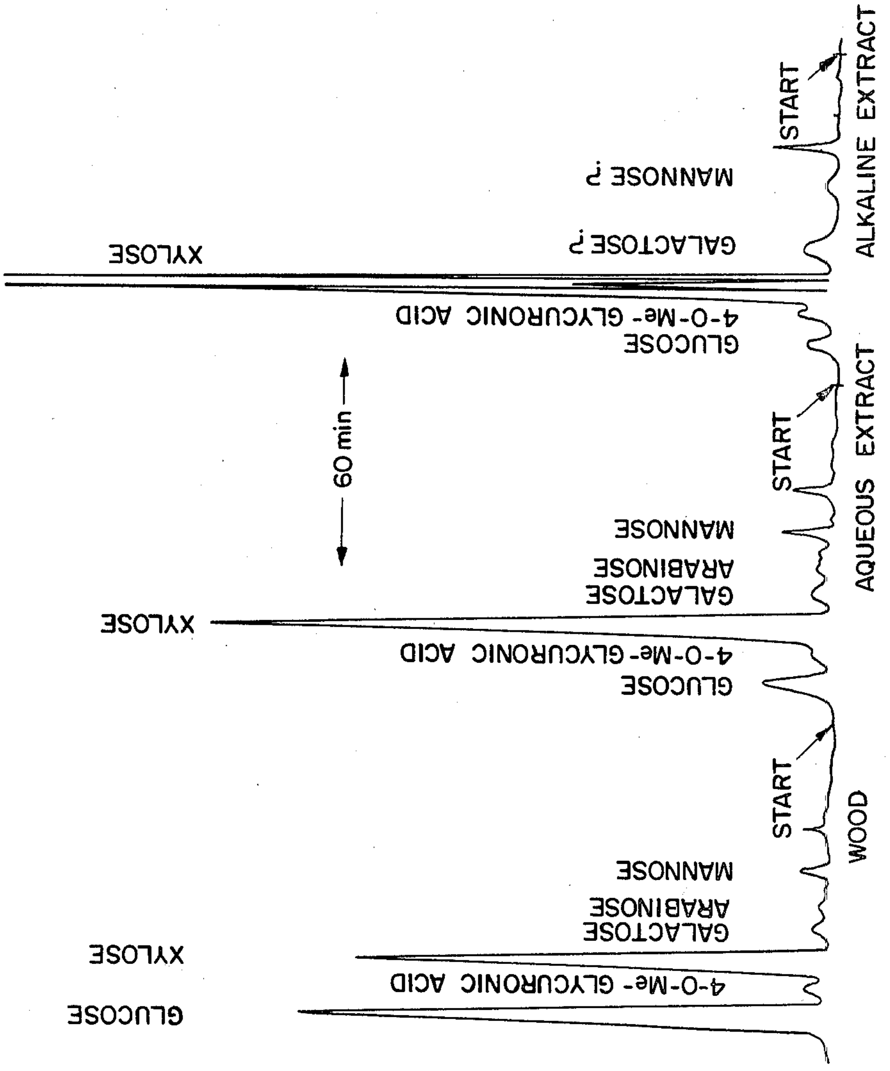

This invention relates to a process for the production of xylose by enzymatic hydrolysis of xylans, as well as to a process for the production of purified enzymes bonded to a carrier which are suitable for said enzymatic hydrolysis.

The use of unmodified soluble enzymes in the saccharification of wood cell wall polysaccharides has been previously described (cf. H. H. Dietrichs: *Enzymatischer Abbau von Holzpolysacchariden und wirtschaftliche Nutzungsmöglichkeiten. Mitt. Bundesforschungsanstalt für Forst- und Holzwirtschaft* 93, 1973, 153–169) as has immobilisation of enzymes on insoluble carriers. Immobilised enzymes are more stable and more easily manipulated than soluble enzymes. However, it should be noted that the use of immobilised enzymes for the saccharification of soluble cell wall polysaccharides has heretofore not been proposed.

Enzymes have previously been used for the hydrolysis of plant cell wall polysaccharides, particularly those derived from culture filtrates of microorganisms (Sinner, M.:*Mitteilungen der Bundesforschungsanstalt für Forst- und Holzwirtschaft Reinbek-Hamburg* No. 104, January 1975, Claeyssens, M. et al FEBS Lett. 11, 1970. 336–338, Reese, E. T. at al *Can. J. Microbiol.* 19, 1973, 1065–1074). These microorganisms produce numerous proteins, including inter alia hemicellulose-splitting enzymes. These free unbonded enzymes, however, are only active for a relatively short time, at most a few days, in optimal reaction conditions. Thus they are unsuited for use on a commercial scale. If attempts are made to add the enzymes from the culture filtrates of microorganisms, i.e. unpurified "raw enzymes", to carrier, substantially all the proteins present in the raw enzyme, i.e. also undesired enzymes, are bonded to the carrier. If it is attemped to convert xylans, e.g. hardwood xylan, into xylose by enzymatic hydrolysis using such enzyme preparations bonded onto carriers, extraordinarily large quantities of such carrier-bonded enzymes are needed because a large proportion of the unnecessary enzymes uselessly occupies large areas of the surface of the carrier, whilst only a small proportion of the added enzymes, namely the exylanolytic enzymes, exhibits the desired catalytic effect.

Processes are known for obtaining certain desired enzymes in purified form from a mixture of enzymes, in which the different electrical charge, molecule size or affinity of the enzymes to an affector is used (see Sinner, M. and H. H. Dietrichs *Holzforschung* 29, 1975, 168–177, Robinsion P. J. et al, *Biotechnol. Bioeng.* 16, 1974, 1103–1112).

It is also known that the breakdown of vegetable, water-soluble, cell-wall polysaccharides to monomeric sugars involves at least two groups of enzymes, namely glycanases, which split the bonds within a polysaccharide at random (with the exception of the bonds at the end of a chain) and glycosidases, which break down the oligosaccharides released by the glycanases into monomeric sugars. Thus, for the breakdown of xylans β-1,4-xylanases and β-xylosidases are necessary. If xylans are present which contain as side groups 4-O-methylglucuronic acid, it is also necessary to use a previously unknown enzyme which splits uronic acid. The two groups of enzyme differ as regards their molecular weight and the conditions in which they develop their optimal activity (see Ahlgren, E. et al, *Acta. Chem. Scandinavia* 21, 1967, 937–944).

An object of the present invention is to provide a process for the preparation of xylose by enzymatic hydrolysis of xylans, which process can be carried out simply, effectively and in high yield, using highly effective enzymes bonded onto carriers. It is a further object of the invention to provide a process for the production of purified enzymes bonded onto carriers, which are suitable for the production of xylose by enzymatic hydrolysis of xylans. Surprisingly it has been found that this object can be simply achieved if various carrier-bonded enzyme systems of differing effect are allowed to act on a solution containing xylans. It has also been found that such enzyme systems can be produced in a very simple manner from raw enzymes by purification and bonding onto a carrier.

According to the present invention there is provided a process for the preparation of xylose by enzymatic hydrolysis of xylan wherein an aqueous xylan-containing solution is treated with:

(a) a carrier having bonded thereto enzymes of the xylanolytic type wherein substantially all of said enzymes are xylanase enzymes, and (b) a carrier having bonded thereto enzymes of the xylanolytic type wherein substantially all of said enzymes are β-xylosidase and, optionally, uronic acid-splitting enzymes.

As stated above, there are uronic acid-containing xylans and xylans which contain no uronic acid. If xylans containing uronic acid are to be enzymatically split according to the invention, the carrier referred to above under (b) must also contain bonded uronic acid-splitting enzyme. If the xylans contain no uronic acid, the uronic acid-splitting enzyme constituent is not required.

In a further aspect of the invention there is provided a process for the production of purified enzymes bonded onto carriers, wherein a raw enzyme preparation containing xylanase, β-xylosidase and, optionally, uronic acid-splitting enzymes is separated by ultrafiltration into one fraction which contains substantially only xylanase enzymes, and a second fraction which contains substantially only β-xylosidase and, optionally, uronic acid-splitting enzymes, and wherein each of the separated fractions is bonded separately to the appropriate carrier.

The process of the present invention provides a highly simple and effective way of producing the monosaccharide xylose in high yield from xylans which are available in large quantities from plant, ie. vegetable, raw materials. Xylose is a valuable sugar which can be used per se or reduced to xylitol, which latter material is also a valuable substance previously relatively difficult to obtain in large quantities.

The xylans or xylan particles used as the starting material for the process according to the invention are hemicelluloses which can be obtained from plant raw materials of various kinds. Examples of such raw vegetable material are hardwood, straw, bagasse, cereal hulls, maize cob residue and maize straw. Plant material which contains xylans principally as hemicelluloses, for example having a xylan content of more than 15%, preferably more than about 25% by weight, is advantageously used to provide the xylan -containing solution utilised in the process according to the invention. The xylan solution can be conveniently obtained by subjecting the xylan-containing plant raw material to steam pressure treatment with saturated steam at temperatures of about 160° to 230° C. for 2 to 240, preferably 2 to 60 minutes, and lixiviating the thermomechanically treated plant raw material with an aqueous solution.

A process for the production of such a xylan solution is described in detail in Austrian Patent Application No. 5346/76 entitled "Process for obtaining xylan and fibrinous materials from xylan-containing raw vegetable matter".

The conditions of xylan hydrolysis by means of carrier-bonded enzymes differ from xylan hydrolysis with free enzymes in that higher temperatures can be selected because of the greater stablility of the bonded enzymes. This allows the hydrolysis to be effected more rapidly. Temperatures in the ragne 30°–60° C., preferably in the range 40°–45° C., generally yield optimal results.

A further advantage of the utilisation of bonded enzymes over free enzymes is that the free enzymes must be used in only a narrow pH band whereas bonded enzymes can be successfully utilised over a much wider pH range. Although the upper and lower limits of the pH band will of course be dependent on the nature of the individual enzyme chosen, in general, the bonded enzymes of the invention can be used at a pH in the range 3 to 8, optimal hydrolytic results being obtained in the range pH 4 to 5. Addition of a suitable buffer to achieve accurate pH control is desirable.

The concentration of the xylans in the solution to be treated can vary within relatively wide limits. The upper limit is determined by the viscosity of the solutions which in turn is determined by the DP (average degree of polymerisation) of the xylans. On average, the upper limit will be about 8%, in many cases about 6%. The lower limit occurs principally because working in too dilute solutions is uneconomic. It is particularly advantageous to use the xylan solutions obtained according to the above-mentioned Austrian Patent Application without further dilution.

The enzymatic hydrolysis is carried out until substantially all the xylans have been broken down into xylose, which can be easily established by analysis of the solution. In this connection, reference is made to the comparison test described later. In the batch process a complete breakdown into xylose can be achieved after about 4 hours.

The process according to the invention can also be carried out in a continuous manner by passing the xylan solution through a column filled with the enzyme preparations used according to the invention. In the column the incubation time can be easily controlled by column dimension and the rate of flow.

Particularly good results are obtained from the process according to the invention using preparations produced according to the process referred to above, i.e. preparations obtained by separating a xylanase, β-xylosidase and, optionally, a uronic acid-splitting enzyme by ultrafiltration into one fraction which contains substantially only xylanase, and one fraction which contains substantially only the β-xylosidase and, where appropriate, uronic acid-splitting enzyme, and bonding these two fractions separately onto carriers. As raw enzymes it is preferable to use culture filtrates of microorganisms which produce these enzymes. Many such microorganisms are known, e.g. *Trichoderma viride, Bacillus pumilus, Varius aspergillus* species and Penicillium species. Raw enzyme preparations obtained from microorganisms are now commercially available, and these can be used in accordance with the invention. Naturally, those preparations which have a particularly high xylanolytic effect are particularly advantageous. Examples of these are Celluzyme 450,000 (Nagase), Cellulase 20,000 and 9 X (Miles Lab., Elkard, Ind., U.S.A.), Cellulase Onozuka P500 and SS (All Japan Biochem. Co., Japan), Hemicellulase NBC (Nutritional Biochem. Co., Cleveland, Ohio, U.S.A.).

Microorganisms which produce a particularly large quantity of enzyme with xylanolytic effect are listed below. Also literature is cited where details of the microorganisms and their optimal culture conditions are set out.

| | | |
|---|---|---|
| *Aspergillus niger* | QM 877 } | for β-xylosidase Reese et al., Can. J. Microbiol. 19, 1973, 1065–1074 |
| *Penicillium wortmanni* | QM 7322 } | |
| *Trichoderma viride* | QM 6 a | for xylanase Reese & Mandels, Appl. Microbiol. 7, 1959, 378–387 |
| | Culture Collection of U.S. Natick Laboratories, Natick, Massachusetts 01760, U.S.A. | |
| *Fusarium roseum* | QM 388 | for xylanase |
| | Philadelphia QM Depot | |
| *Trichoderma viride* | CMI 45553 | for xylanase Gascoigne & Gascoigne, J. Gen. Microbiol. 22, 1960, 242–248 |
| | Commonwealth Mycological Institute, Kew | |
| *Fusarium moniliforme* | CMI 45499 | for xylanase |
| *Bacillus pumilus* | PRL B 12 | for β-xylosidase Simpson, F. J., Canadian J. Microbiol. 2, 1956, 28–38 |
| | Prairie Regional Laboratory Saskatoon, Saskatchewan, Canada | |
| *Coniophora cerebella* | | for xylanase King, Fuller, Biochem. J. 108, 1968, 571–576 |
| | F.P.R.L. culture no. 11 E Forest Products Research Laboratory Princes Risborough, Bucks. | |
| Bacillus No. C-59-2 | | for xylanase extremely thermostable |

-continued

| | |
|---|---|
| | broad pH optimum<br>2-day culture |
| | Institute of Physical and Chemical Research<br>Wako-shi, Saitama 351<br>K. Horikoshi & Y. Atsukawa,<br>Agr. Biol. Chem. 37, 1973,<br>2097–2103 |

Further details regarding microorganisms with strong xylanolytic enzymes can be found in the following literature:

| | |
|---|---|
| β-xylosidases | |
| *Aspergillus niger* | |
| Botryodiplodia sp. | Reese, E.T. et al, Can. J. Microbiol. 19, 1973, 1065–1074 |
| *Penicillium wortmanni* | |
| *Chaetomium trilaterale* | Kawaminami, I. & H. Izuka, J.Ferment.Technol. 48, 1970, 169–176 |
| *Bacillus pumilus* | Simpson, F.J., Can.J. Microbiol. 2, 1956, 28–38 |
| β-1→4-xylanases | |
| *Trichoderma viride* | Reese, F.T. & M. Mandels, Appl. Microbiol. 7, 1959, 378–387<br>Nomura, K. et al, J. Ferment. Technol. 46, 1968, 634–640<br>Takenishi, S. et al, J. Biochem. (Tokyo) 73, 1973, 335–343 |
| *A. batatae* | Fukui, S. & M. Sato, Bull.agric. chem.soc.Japan 21, 1957, 392–393 |
| *A. oryzae* | Fukui, S. J.Gen.Appl.Microbiol. 4, 1958. 39–50 |
| *Fusarium roseum* | Gascoigne, J.A. & M.M. Gascoigne, J.Gen.Microbiol. 22, 1960, 242–248 |
| *P. Janthinellum* | Takenishi, S. & Y. Tsujisaka, J. Ferment. Technol. 51, 1973, 458–463 |
| *Chaetomium trilaterale* | Iizuka, H. & Kawaminami, Agr.Biol. Chem. 33, 1969, 1257–1263 |
| *Coniophora cerebella* | King N.J., Biochem.J. 100, 1966 784–792 |
| Trametinae | Kawai, M. Nippon, Nogei Kagaku Kaishi, 47, 1973, 529–34 |
| Coriolinae | (from a screening test under basidiomycetes) |
| Lentinae | |
| Tricholomateae | |
| Coprinaceae | |
| Fomitinae | |
| Polyporinae | |
| Bacillus No. C-59-2 | Horikoshi, K. & Y. Atsukawa, Agr. Biol. Chem. 37, 1973, 2097–2103 |
| *Streptomyces xylophagus* | Iizuka, H. & T. Kawaminami, Agr. Biol.Chem. 29, 1965, 520–524 |
| *Bacillus subtilis* | Lyr, H., Z. Allg.Mikrobiol. 12, 1972, 135–142 |

The carrier-bonded purified enzymes used according to the invention are preferably produced by removing the insoluble particles of a raw enzyme solution, conveniently by normal filtration, filtering the solution through an ultrafilter having a cut-off of from about MW 80,000 to about MW 120,000, preferably about MW 100,000, filtering the supernatant through an ultrafilter with a cut-off of from about MW 250,000 to about MW 350,000, preferably about MW 300,000. The filtrate thus obtained, which principally contains β-xylosidase and possibly uronic acid-splitting enzymes, in bonded onto a carrier. The filtrate from the ultrafiltration with the separating range first referred to above is filtered through an ultrafilter with cut-off of from about MW 10,000 to about MW 50,000, preferably about MW 30,000 and the filtrate thus obtained, which principally contains xylanase, is bonded onto a carrier. In order to carry out this process it is advisable to dissolve the raw enzyme in approximately 10 to 30 times, preferably about 20 times, the amount of water.

A greater degree of purification of the fraction principally containing xylanase can be achieved by filtering the filtrate after filtration through an ultrafilter with a cut-off of about MW 10,000 to 50,000 through an ultrafilter with a cut-off range of from about MW 300 to about MW 700, preferably about MW 500, and bonding the residue onto a carrier. The xylanase is concentrated by this additional ultrafiltration. Simultaneously, the greater part of the carbohydrates, which can constitute up to about 40% of the starting material, is eliminated in the ultrafiltrate.

In relation to this invention, when the words "principally" or "substantially" are used in connection with the specified enzymes, it should be understood that the enzymes contained in the fraction concerned with regard to xylanolytic effect consist substantially of the enzymes specified or that the fraction concerned principally contains the specified enzyme as enzyme. After the purifying operation has been carried out a fraction for example of xylanase is obtained in which there is practically no perceptible β-xylosidase content. The same applies in reverse to the β-xylosidase fraction.

Within the framework of the invention, particularly for carrying out the process for production of xylose by enzymatic hydrolysis of xylans, it is however possible to use carriers which do not have such a high degree of purity of the respective enzyme. For example, the advantageous results according to the invention are also obtained when by the term "principally" or "substantially" it is understood that the enzyme concerned provides at least about 80%, preferably at least about 90%, and most preferably about 95% of the desired main activity.

It is surprising that by means of simple ultrafiltration it is possible to separate the raw enzyme into the desired components, which are thus obtained with a high degree of purity. It is also surprising that the uronic acid-splitting enzyme is also contained in the fraction containing the β-xylosidase. Xylanase and β-xylosidase alone are not capable of splitting the acid xylan fragments, which may also be produced in the breakdown solution by the action of the xylanase on the xylan chain, into monomeric xylose. The acid xylooligomers must first be freed from the acid residue by the catalytic action of the uronic acid-splitting enzyme before they can be further hydrolysed to form xylose.

The bonding of the purified enzyme fractions on to carriers is carried out by processes which are known per se. Various bonding processes are known which differ according to the type of bonding (adsorption, covalent bonding onto the surface of the carrier, covalent transverse cross-linking, inclusion, etc.) and degree of difficulty and expense of producing the bond. Those processes which ensure a lasting bond (covalent bonding) keep diffusion hindrances to a minimum in high molecular weight substrates and can be easily carried out are preferred. The following have proved particularly advantageous according to the invention:

1. Bonding via glutaraldehyde (Weetall, H. H., *Science* 166, 1969, 615–617),
2. Bonding via cyclohexylmorpholinoethyl-carbodiiimide-toluenesulfonate (CMC), Line, W. F. et al, *Biochim. Biophys. Acta* 242, 1971, 194–202),
3. Bonding via $TiCl_4$ (Emery, A. N. et al, *Chem. Eng. (London)* 258, 1972, 71–76).

Any carrier conventionally used in this field may be used in the process of the invention. A non-exhaustive list of carriers includes steel dust, titanium oxide, feldspar and other minerals, sand, kieselguhr, porous glass, silica gel and the like. An example of a porous glass carrier is that sold under the trade name "CPG-550" (Corning Glass Works, Corning, N.Y., U.S.A.) and an example of a suitable silica gel carrier is that sold under the trade name "Merckogel SI-1000" (Merck AG, Darmstadt, West Germany). For production of the carrier-enzyme bond according to methods 1 and 2 it is advantageous to heat the carriers overnight under reflux with about 5% to 12%, preferably about 10% γ-aminopropyltriethyloxysilane in toluene. This provides the carrier material with a primary amino group. This step is not necessary with method 3.

After extensive washing with suitable solvents such as toluene and acetone the carrier is activated. This step consists in method 1 of stirring the carrier in about 3% to 7%, preferably about 5%, glutaraldehyde solution of the bonding buffer. A buffer pH of 6.5 has proved more favourable than a buffer pH of pH4. The higher the bonding pH, the more protein is bonded. Since the enzymes are stable in the slightly acid range, a pH of 6–7.5, preferably 6.5, is suitable for the bonding.

After 60 minutes incubation, partly under vacuum, it has proved advantageous to draw off the surplus glutaraldehyde solution. It is then advisable to wash the carrier material thoroughly before it is incubated wit the enzyme solution.

In method 2 the alkylamine carrier is stirred well for 5 minutes with the enzyme to be bonded before the CMC reagent which starts the bonding is added. If too great a quantity of CMC is added there is a danger of cross-linking resulting in loss of activity of the enzyme. With 1 g of carrier and 150 mg of enzyme it is preferable to use about 350 to 450 mg, preferably about 400 mg, of CMC. During the first 30 minutes of incubation the pH can conveniently be held at 3 to 5, preferably about 4.0, with 0.1 N HCl. This pH value has proved more advantageous than a pH value of 6.5. The CMC method and the $TiCl_4$ method are particularly suitable for enzymes which are stable in the acid range. The highest quantities of protein are bonded in the acid range.

In method 3 activation of the carrier is achieved by stirring the untreated carrier in about 6 to 15%, preferably 12.5%, aqueous $TiCl_4$ solution. Surplus water is evaporated off and the reaction product is dried at 45° C. in a vacuum drying cabinet. Finally, it is thoroughly washed with the bonding buffer before being incubated with the enzyme solution to be bonded.

Incubation of the activated carrier with the enzyme solution is complete after several hours, e.g. overnight. The duration of the incubation is not particularly critical. Incubation is conveniently carried out at normal or ambient temperatures.

After the bonding process the carrier-bonded enzyme preparations are washed over a frit with 1 M NaCl in 0.02 M phosphate buffer pH4 and then with 0.02 M phosphate buffer pH5 until no more enzyme can be found in the washings.

According to the process of the invention an extraordinarily extensive purification of those enzymes necessary for the breakdown of the xylans is carried out. In this way carriers are obtained with an extraordinarily high specific catalytic activity and the enzymatic hydrolysis of xylans is advantageously effected. It is particularly surprising, as demonstrated by the comparison tests described below, that the yield of xylose according to the process of the invention is considerably greater than would be the case if xylanase, β-xylosidase and, where appropriate, a uronic acid-splitting enzyme had been bonded all together onto one carrier and it had been attempted to carry out the enzymatic hydrolysis of xylans by using this carrier containing all three enzymes to act on the aqueous xylan solution.

In the specification and in the Examples percentages are percentages by weight unless otherwise stated. The obtaining, isolation and purification of the desired substances present in solution is carried out, so far as is convenient, according to processes usual in the field of sugar chemistry, e.g. by concentration of solutions, mixing with liquids in which the desired products are not or only slightly soluble, recrystallisation, etc.

Example 1

Decomposition Process 400 g of red beech wood in the form of chips, air-dry, were treated in an Asplund Defibrator with steam for 6 to 7 minutes at 185°–190° C., corresponding to a pressure of about 12 atmospheres, and defibrated for about 40 seconds. The damp fibrous material thus obtained was rinsed out of the defibrator with a total of 4 l of water and washed on a sieve. The yield of fibrous material amounted to 83% in relation to the wood used (absolutely dry).

The washed and pressed fibrous material was then suspended in 5 l of 1% aqueous NaOH at room temperature and after 30 minutes was separated from the alkaline extract by filtration and pressing. After washing with water, dilute acid and then again with water the yield of fibrous material amounted to 66% in relation to the wood used (absolutely dry).

Other types of wood, also in the form of coarse sawdust such as chopped straw, were treated in a similar manner. The mean values for the yields of fibrinous materials in relation to the starting materials (absolutely dry) amounted to:

| | Fibrous material residue (%) | |
|---|---|---|
| Starting material | after washing with $H_2O$ | after treatment with NaOH |
| Red Beech | 83 | 66 |
| Poplar | 87 | 71 |
| Birch | 86 | 68 |
| Oak | 82 | 66 |
| Eucalyptus | 85 | 71 |
| Wheatstraw | 90 | 67 |
| Barley straw | 82 | 65 |
| Oat straw | 88 | 68 |

EXAMPLE 2

Carbohydrate Composition of the Aqueous and Alkaline Extracts

Aliquot proportions of the aqueous and alkaline extracts obtained by the process of Example 1 were subjected to total hydrolysis. The quantitative determination of the individual and total sugars was carried out with the aid of a Biotronic Autoanalyser (cf. M. Sinner, M. H. Simatupang & H. H. Dietrichs, *Wood Science and Technology* 9, (1975) P. 307–322). In the autoanalyser the wood subjected to total hydrolysis was examined. FIG. 1 shows the diagram obtained for red beech.

| | Dissolved Carbohydrate | | |
|---|---|---|---|
| | Total (% in relation to starting material | Fractions (% in relation to extract) | |
| Extract | absolutely dry) | Xylose | Glucose |
| Red Beech $H_2O$ | 13.5 | 69 | 13 |
| NaOH | 7.0 | 83 | 3 |
| Oak $H_2O$ | 13.2 | 65 | 11 |
| NaOH | 6.8 | 81 | 5 |
| Birch $H_2O$ | 11.2 | 77 | 8 |
| NaOH | 7.3 | 84 | 3 |
| Poplar $H_2O$ | 8.3 | 76 | 6 |
| NaOH | 6.5 | 83 | 3 |
| Eucalyptus $H_2O$ | 9.5 | 71 | 8 |
| NaOH | 5.0 | 80 | 3 |
| Wheat $H_2O$ | 7.0 | 53 | 21 |
| NaOH | 8.3 | 88 | 3 |
| Barley $H_2O$ | 6.1 | 41 | 25 |
| NaOH | 9.5 | 88 | 3 |
| Oats $H_2O$ | 5.1 | 44 | 20 |
| NaOH | 4.4 | 88 | 3 |

EXAMPLE 3

Separation and Concentration of Xylanase and β-Xylosidase from a Commercial Enzyme Preparation 200 g of the raw enzyme preparation "Celluzyme" commercially available from the firm Nagase were dissolved in 4.8 l of 0.02 M AmAc buffer (ammonium acetate buffer) pH5. The insoluble residue was partly removed with a frit. The enzyme solution was then clear filtered through a Teflon filter (Chemware 90 CMM Coarse). This was followed by ultrafiltration of the enzyme solution on the ultrafiltration appliance TCF-10 made by Amincon (Lexington, Mass., U.S.A.).

The following Amincon Ultrafilters were used (in order of use:

XM 100 A: (Separating range MW 100,000)
XM 300: (Separating range MW 300,000)
PM 30: (Separating range MW 30,000)
DM 5: (Separating range MW 500)

The purified raw enzyme solution was then filtered through an ultrafilter with a cut-off of MW 100,000. The xylanase was predominantly present in the ultrafiltrate. The β-xylosidase and a hitherto unknown enzyme which is responsible for the splitting of the 4-O-methylglucuronic acid of acid xylooligomers were predominantly present in the supernatant.

The supernatant from this ultrafiltration was then filtered through an ultrafilter of MW 300,000 cut-off. At the end of this treatment the β-xylosidase, together with the uronic acid-splitting enzyme activity, was only perceptible in the clear solution of the ultrafiltrate, whereas the thick dark brown supernatant had no β-xylosidase activity and no uronic acid-splitting activity.

The filtrate obtained in the first ultrafiltration was treated in the following manner:

Ultrafiltration on PM 30: After this step the xylanase was in the ultrafiltrate. Non-xylanase-active substances remained in the supernatant.

Ultrafiltration on DM 5: The xylanase was in the supernatant; it was concentrated by this step. Simultaneously the greater part of the carbohydrate (in the starting material 39%) was eliminated by passing in the ultrafiltrate.

In the following Table the activities of xylanase, β-xylosidase and uronic acid-splitting enzyme are given. The values given are in "units". 1 unit is the quantity of enzyme which increases the sugar content of the substrate solution (1% beechwood xylan for xylanase, 2 mMol p-nitrophenylxylopyranoside for β-xylosidase, 0.2 μg/μl 4-O-methylglucuronosylxylotriose for the acid-splitting enzyme) at 37° C. by 1 μMol xylose for xylanase and β-xylosidase and 1 μMol 4-O-methylglucuronic acid for the uronic acid-splitting enzyme.

| | Xylanase | β-xylosidase | Glucuronic acid splitting activity |
|---|---|---|---|
| Celluzyme dissolved | 34,560 U | 1541 U | 2568 U |
| XM 100 A residue | 7,968 U | 1290 U | 1996 U |
| XM 100 A Ultrafiltr. | 24,480 U | 13 U | 524 U |
| XM 300 Ultrafiltr. | — | 1011 U | 1817 U |
| PM 30 Ultrafiltr. | 21,173 U | | |
| DM 5 residue | 19,730 | | |

The activities were measured by the following processes:

The xylanase with beechwood xylan as substrate was determined reductometrically (SUMNER, of. HOSTETTLER, F., E. BOREL & H. DEUEL, *Helv. Chim. Acta* 34, 1951, 2132–39). For measurement of the β-xylosidase activity a p-nitrophenylxyloside solution diluted to 1.5 ml was mixed after incubation with 2 ml 0.1 M borate buffer pH 9.8. The extinction of the liberated p-nitrophenol was determined directly at 420 nm. The quantity of p-nitrophenol was read off on a calibration curve and converted into xylose. 4-O-methylglucuronosylxylotriose served as substrate for the uronic acid-splitting enzyme. after the reaction the solution was analysed by column chromatography on Durrum DA X-4. (SINNER, M., M. H. SIMATUPANG & H. H. DIETRICHS, *Wood Sci. Technol.* 9, 1975, 307–22). The liberated quantity of 4-O-methylglucuronic acid was calculated in μMol/min.

EXAMPLE 4

Deposition of the Enzymes on the Carrier

Porous glass "CPG-550" (Corning Glass Works, Corning, N.Y., U.S.A.) was chosen as the enzyme carrier. The xylanolytic enzymes were bonded on to the enzyme carrier via glutaraldehyde (WEETALL, H. H., *Science* 166, 1969, 615–17).

1 g of the porous glass used as carrier was heated overnight with 10% aminopropyltriethyloxysilane in toluene at reflux temperature. This provided the carrier with a primary amino group. It was then washed thoroughly with toluene and acetone. Afterwards the carrier was stirred with 20 ml of a 5% glutaraldehyde solution in a 0.02 M phosphate buffer at pH 6.5. Stirring was carried out for 15 minutes in a vacuum (300 torr) followed by further incubation for 45 minutes at normal pressure. Drawing off followed and the carrier material was thoroughly washed with 200 ml buffer.

Using this activated carrier material, two carrier-bonded enzyme preparations were produced:

(a) 1 g of the activated carrier was stirred overnight with 5 ml of xylanase solution (657 units) obtained according to Example 3. It was then washed over a frit with 1 M NaCl in 0.02 M phosphate buffer pH4 and then 0.02 M phosphate buffer pH5, until no enzyme was perceptible in the washings.

The preparation thus obtained contains 64 units of active xylanase bonded per g.

(b) The process described in (a) above was repeated, except that 5 ml of the solution obtained according to Example 3 was used, containing 33 units β-xylosidase and 60 units uronic acid-splitting enzymes. The preparation 2 thus obtained contained about 33 units β-xylosidase and 60 units uronic acid-splitting enzyme bonded per g.

EXAMPLE 5

Figure 2:
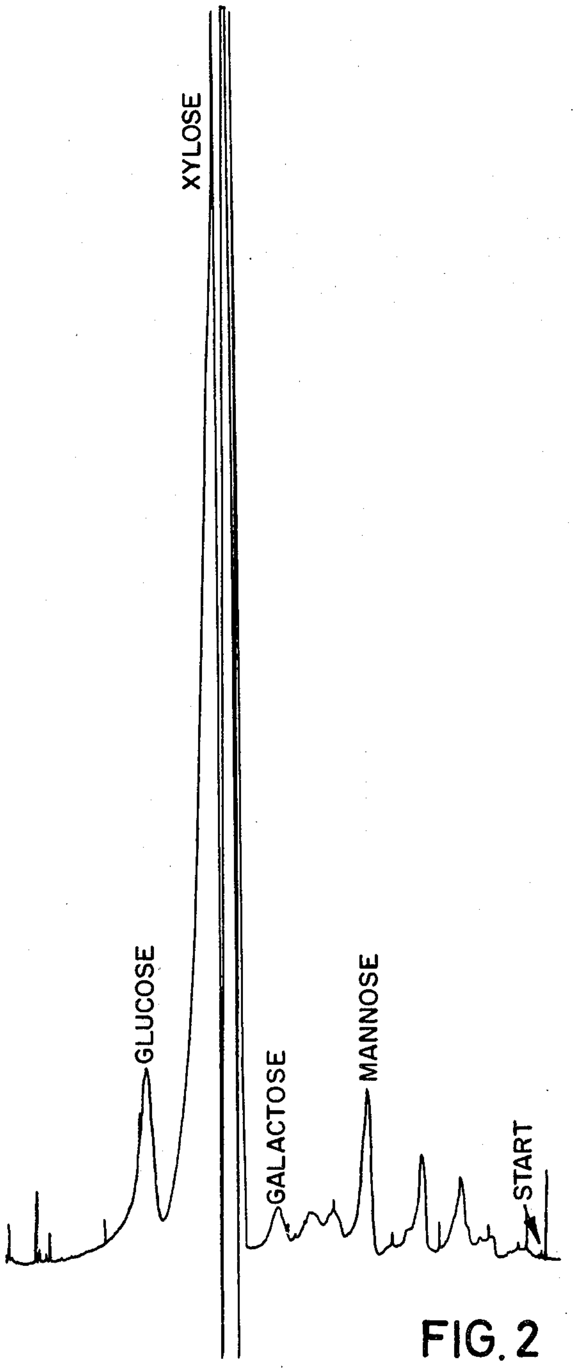

Hydrolysis of Beechwood Xylan 2 ml of the xylan solution from the thermomechanical treatment of beech wood obtained according to Example 1 by washing with water (the solution contains 1.3% xylan) were incubated with 60 mg of preparation 1 and 60 mg of preparation 2 obtained according to Example 4 at 40° C. in a shaking water bath. The hydrolysis of the xylan was analysed by column chromatography using an ion exchange resin (commercial product Durrum DA X-4 made by Durrum) (SINNER, M., M. H. SIMATUPANG & H. H. DIETRICHS, *Wood Sci. Technol.* 9, 307–22). After four hours the beech wood xylan was hydrolysed to its monomeric components xylose and 4-O-methylglucuronic acid. FIG. 2 shows the chromatograph after four hours' incubation. It can be seen from this that complete breakdown of the xylan to xylose occurred in the solution. The solution contains no xylobiose. In the Figure the abbreviation GlcA stands for 4-O-methylglucuronic acid.

COMPARISON TESTS

The process was carried out as in Example 5 but an enzyme preparation produced as in Example 4 was used and the enzyme solutions containing the xylanase as well as the β-xylosidase and the uronic acid-splitting enzyme were bonded together onto one carrier. Two ml of the xylan solution used in Example 5 were incubated at 40° C. with 60 mg of the preparation containing xylanase, β-xylosidase and the uronic acid-splitting enzyme.

In a further comparison test the same process was carried out but only 60 mg of preparation 1 produced according to Example 4 were used (carrier-bonded xylanase).

Figure 3:
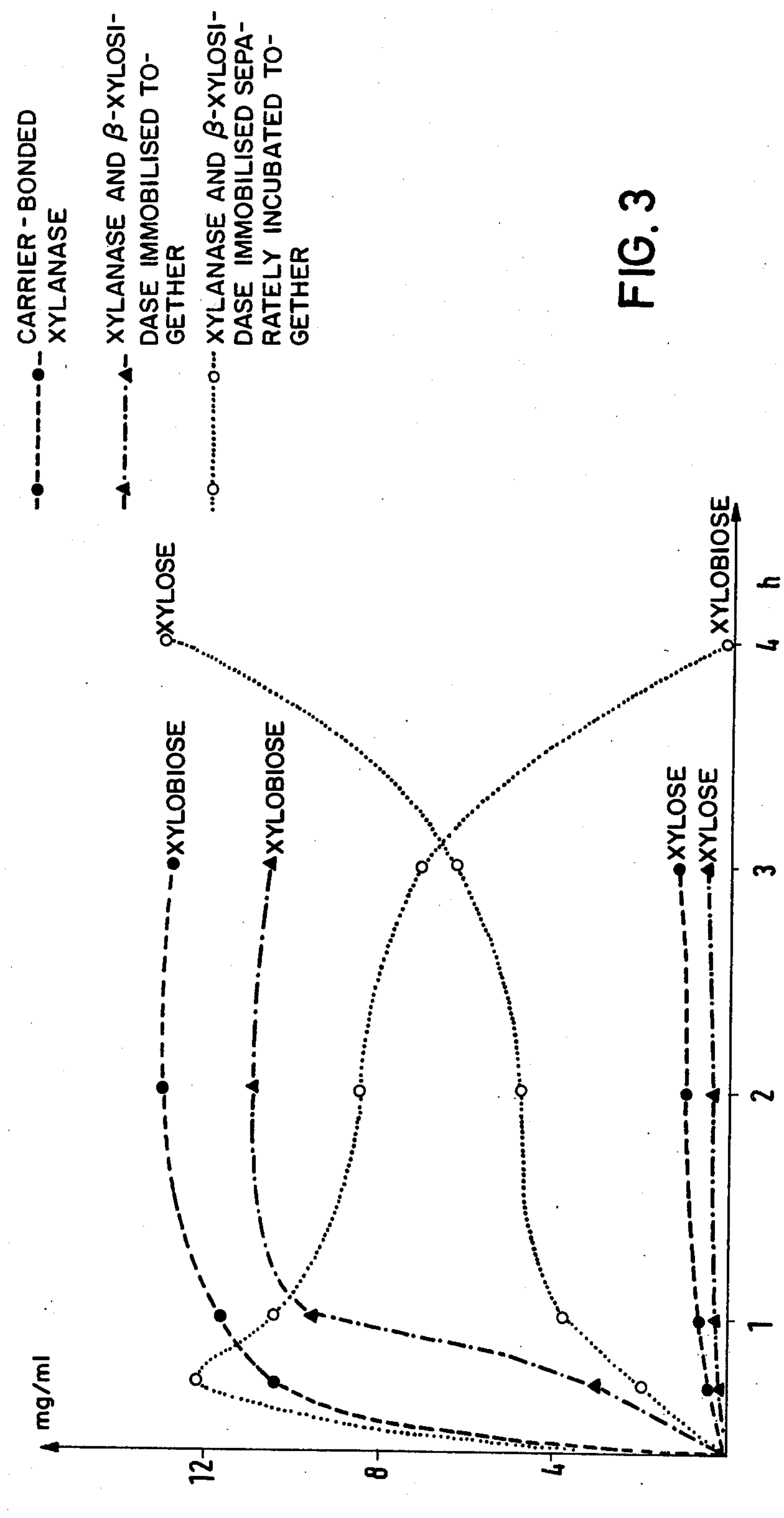

The xylan breakdown of the two solutions was carried out as described in Example 5 for over three hours by column chromatography. The xylobiose and xylose content of the solutions is shown in FIG. 3. This Figure also shows the xylobiose and xylose content of the solution of Example 5 (xylanase and β-xylosidase as well as uronic acid-splitting enzyme immobilised separately, incubated together). From FIG. 3 the following can be seen:

The enzymes immobilised together had already hydrolysed a large proportion of xylan present (13 mg/ml) to xylobiose. After 1 hour, the concentration of the desired final breakdown product xylose did not increase further when the incubation time was increased.

The carrier-bonded xylanase had already broken down most of the xylan present to oligomeric sugars after 30 minutes. The xylose content naturally did not increase since the final neutral breakdown produce of xylanase is substantially xylobiose.

The enzymes of Example 5, i.e. enzymes immobilised separately but incubated together according to the invention, had broken down the xylan solution after 30 minutes to xylobiose and xylose and acid sugars. With increased incubation time the xylose concentration increased through the action of the β-xylosidase, correspondingly the xylobiose content of the reaction solution decreased. After 4 hours total hydrolysis to xylose and 4-O-methylglucuronic acid was achieved as can be seen from FIG. 2 (cf. Example 5).

We claim:

1. A process for the preparation of xylose by enzymatic hydrolysis of xylan comprising treating an aqueous solution containing the xylan with:

(a) a first carrier having bonded thereto enzymes of the xylanolytic type wherein substantially all of said enzymes are xylanase enzymes, and (b) a second carrier having bonded thereto enzymes of the xylanolytic type wherein substantially all of said enzymes are selected from the group consisting of β-xylosidase and β-xylosidase and uronic acid-splitting enzymes and hydrolyzing said treated solution.

2. A process according to claim 1, wherein the aqueous xylan-containing solution is derived from the steam pressure treatment of xylan-containing plant raw material at a temperature of from 160° to 230° C. for from 2 to 240 minutes with attendant defibration followed by lixiviation of the thus-decomposed vegetable raw material with an aqueous solution.

3. A process according to claim 1, wherein the enzymes bonded onto the carriers are prepared by ultrafiltration of a raw enzyme preparation containing xylanase, and β-xylosidase enzymes; the ultrafiltration separating the xylanase enzymes into one fraction and the β-xylosidase enzymes into a second fraction and wherein each of the two separated fractions is bonded separately to the appropriate carriers.

4. A process according to claim 3, wherein the untreated enzyme is dissolved in a buffered solution having a pH of about 4 to 6, and freed of insoluble constituents, the solution is filtered through an ultrafilter with a cut-off of from MW 80,000 to MW 120,000, the supernatant is filtered through an ultrafilter having a cut-off of from MW 250,000 to MW 350,000, and the filtrate containing substantially all β-xylosidase enzyme is bonded onto the second carrier, the filtrate from the first ultrafiltration is filtered through an ultrafilter having a cut-off of from MW 10,000 to MW 50,000 and the filtrate containing substantially all xylanase is bonded onto the first carrier.

5. A process according to claim 4, wherein the filtrate containing principally xylanase enzyme is filtered through an ultrafilter with a cut-off of from MW 300 to MW 700 and the supernatant is bonded onto the carrier.

6. A process according to claim 3, wherein the carrier is activated with glutaraldehyde, cyclohexylmorpholinoethyl-carbodiimide-toluenesulfonate or $TiCl_4$.

7. The method of claim 3 wherein the raw enzyme also contains uronic acid-splitting enzymes which are separated into the second fraction by ultrafiltration along with the β-xylosidase.

8. The process of claim 4 wherein the untreated enzyme contains uronic acid-splitting enzymes which are separated into the filtrate with the β-xylosidase with the first ultrafiltration and bonded onto the carrier with the β-xylosidase.

* * * * *